United States Patent [19]
Marran

[11] Patent Number: 5,792,127
[45] Date of Patent: Aug. 11, 1998

[54] URINE COLLECTION AND DRAINAGE DEVICE

[76] Inventor: James E. Marran, 213 E. Highland Ave., Atlantic Highlands, N.J. 07716

[21] Appl. No.: 735,842

[22] Filed: Oct. 23, 1996

[51] Int. Cl.[6] ................................................ A61F 5/44
[52] U.S. Cl. ........................ 604/353; 604/327; 604/331
[58] Field of Search ................................. 604/323, 327, 604/331, 329, 349, 351, 353

[56] References Cited

U.S. PATENT DOCUMENTS

| | | | |
|---|---|---|---|
| 3,547,123 | 12/1970 | Sachs | 128/298 |
| 3,601,125 | 8/1971 | Moss | 128/295 |
| 4,073,295 | 2/1978 | Laufbahn | 128/295 |
| 4,449,971 | 5/1984 | Cawood | 604/54 |
| 4,511,358 | 4/1985 | Johnson, Jr. et al. | 604/327 |
| 4,581,763 | 4/1986 | Olsen | 604/323 |
| 4,846,816 | 7/1989 | Manfredi | 604/323 |
| 4,901,375 | 2/1990 | Dahlgren | 4/144.3 |
| 5,053,027 | 10/1991 | Manfredi | 604/327 |

*Primary Examiner*—Robert A. Clarke
*Attorney, Agent, or Firm*—Thomason & Moser

[57] ABSTRACT

A urine collection and drainage device comprising a chamber that contains a baffle. The device minimizes noises generated from sloshing urine in the chamber. Furthermore, when secured in a horizontal orientation relative to an individual's leg, the device is completely concealed from view by others while worn under shorts, short skirts or swimming trunks. Thus, the device collects urine such that it baffles any sloshing noises that emanate from the chamber and is completely concealed from view when worn under summer or sport apparel.

9 Claims, 1 Drawing Sheet

URINE COLLECTION AND DRAINAGE DEVICE

BACKGROUND OF THE DISCLOSURE

1. Field of the Invention

The invention relates to a urine collection and drainage device. More specifically, the invention relates to a non-sloshing urine collection and drainage device that can be comfortably worn and concealed while wearing sport or summer apparel.

2. Description of the Background Art

Urine collection and drainage devices are used by individuals, i.e., men and women with urinary incontinence. Although a common problem in both genders, urinary incontinence is a condition that causes much discomfort and distress for incontinent individuals. Conventionally, whether the incontinence results from a blockage of the urinary tract or a failure to control urine flow, an invasive urinary bladder drainage catheter, having a long extension tube, is fitted internally into the bladder. The catheter is usually inserted through the urethra of the urinary incontinent individual. Alternatively, the catheter can be inserted in the bladder through a cystotomy opening. Extending externally, the long extension tube is attached to a urine collection and drainage device. Instead of an invasive catheter, a non-invasive device can be used to cover the urethral opening of the incontinent individual to funnel the flow of urine. Likewise, the non-invasive device communicates with the urine collection and drainage device via a long extension tube.

Urine storage and emptying devices vary in design. The most basic designs of urine collection devices consist of a bag or a bottle for collecting volumes of urine. The bag or bottle is affixed to the end of the long extension tube. The bag or bottle is either carried by the individual or placed on a support located nearby the individual. This type of urine collection device restricts the individual's freedom of movement and makes concealment of the device under the individual's clothing impractical. The unsubtle exposure of the urine collection device places incontinent individuals in an embarrassing situation causing much distress and anxiety.

Other designs secure the device directly to the incontinent individual, either to the waist or the lower leg. These designs incorporate waist belts and elastic straps to secure the urine collection device to the individual. Such urine collection devices are perverse to concealment under sport and summer apparel. However, while these designs improve the individual's freedom of movement from the most basic designs, the waist belt and straps of the waist belt and lower leg designs further discomfort the wearer by irritating the wearer's skin. Additionally, "sloshing" sounds emanating from collected urine in all of the prior urine collection devices are audible to the wearer and to people nearby the wearer. These sloshing noises can be embarrassing to the incontinent individual.

Therefore, there is a need in the art for a non-sloshing urine collection and drainage device that is fully concealed while comfortably secured to an incontinent individual while worn under summer or sporting apparel.

SUMMARY OF THE INVENTION

The disadvantages associated with the prior art are overcome by an inventive urine collection and drainage device for use by an individual, i.e., a man or a woman, with urinary incontinence. In general, urine collection devices limit the types of activities an individual wearing such a device could engage in. The inventive device increases the individual's freedom of movement.

More specifically, the device contains a collection chamber with baffles. Such baffles minimize noises generated from sloshing urine in the collection chamber. Furthermore, when secured in a horizontal orientation relative to an individual's upper leg, the device is completely concealed from view by others while worn under shorts, short skirts or swimming trunks. Thus, the device collects urine such that it is completely concealed from view under summer/sport apparel and baffles sloshing noises emanating from the splashing urine in the chamber.

BRIEF DESCRIPTION OF THE DRAWINGS

The teachings of the present invention can be readily understood by considering the following detailed description in conjunction with the accompanying drawing in which.

DETAILED DESCRIPTION

Figure 1:
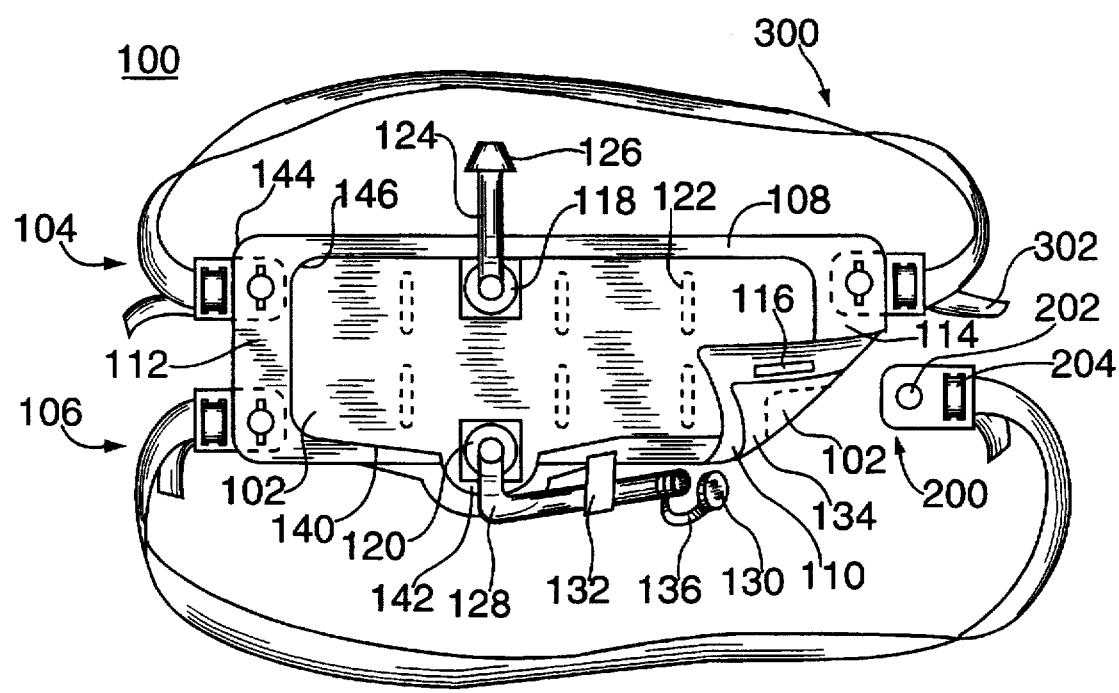
FIG. 1 depicts a perspective view of a non-sloshing urine collection and drainage device.

The present invention is a non-sloshing urine collection and drainage device. When worn by an individual, i.e., a man or a woman, the device can be concealed underneath sport or summer apparel. The device collects urine while connected to a urine conduit that is attached, either invasively or externally, to the individual.

More specifically, the invention comprises a chamber with baffles that prevent sloshing of the collected urine. An individual wearing the device under shorts, short skirts, swimming trunks, etc., can engage in physical activities without the anxieties of having urine leakage or of visually or audibly exposing the device to others.

FIG. 1 depicts a perspective view of a non-sloshing urine collection and drainage device 100 comprising a chamber 102 with baffles 122. The device is secured to an individual by a combination of adjustable buckles 200 and straps 300. The adjustable buckles 200 have buttons 202 that are removably engaged through button slots 116 in securing flange, 112 and 114, extending from either side of the chamber 102. To comfort the individual wearing the device and to improve securing the device to the individual, the device has a cloth 134 adhered to the back side 110. To further comfort the individual wearing the device, the device has rounded corners 144. The chamber 102 has an intake opening 118 on the front side 108 near the top 104 of the chamber. An intake valve 124 has a connector 126 that adjustably connects to urine conduits. Urine travels from the individual's bladder through the attached conduit and into the chamber of the device via the intake valve 124 and intake opening 118. The collected urine in the chamber 102 is directed by sloping portions 140 and a drain catch 142 towards a drain opening 120 near the bottom 106 of the chamber. Urine is emptied from the chamber through a drain valve 128 that is attached to the drain opening. The flow of draining urine is further controlled by the individual with a drain clamp 132 and a drain cap 130 on the drain valve 128.

The non-sloshing urine collection and drainage device 100 has dimensions that allow a wearer to conceal the device under clothing. Preferably, the dimensions of the device are such that the device is concealed under summer or sport apparel, such as shorts, short skirts, swim suit, etc., when worn horizontally on the upper leg of the individual. Thus, the overall size of the device should have a horizontal length of approximately 10 inches, and a vertical height of approximately 5 inches. Any variation of length or height could be implemented, so long as the device would be concealed under summer or sport clothing. Additionally, the placement of the device on the individual is relative to the bladder. The device can be placed anywhere below the bladder because urine flow is gravity generated.

Typically, the chamber 102 is formed of soft pliable plastic material. Two sheets, an upper/front sheet 108 and a lower/back sheet 110, of the plastic material are superimposed and the edges are heat sealed. Preferably, the chamber corners 146 and other chamber elements are rounded to prevent sloshing of the collected urine. Baffles 122 are formed during the heat sealing process of the chamber 102. Preferably, the baffles 122 are formed by intermittently bonding the front 108 and back 110 sheets to one another. The length and number of baffles can be any size or number. Preferably, there are six baffles, i.e., three sets of two baffles. Each baffle preferably has a length of approximately one and a three-quarter inches with a width of approximately a sixteenth of an inch. Each set of two is equally spaced apart from one another in the collection chamber. The two baffles in each set are spaced vertically above and below each other with a gap of approximately one inch between each of the baffles.

The edges of the bag are reinforced by a heat-sealed band. At either end of the chamber, along the entire vertical length of the chamber, the plastic material is strengthened and sealed forming securing flange, 112 and 114. One or more button slots 116, preferably two, are formed in each securing flange, 112 and 114.

At the top 104, and preferably on the front 108 of the chamber 102, an intake opening 118 is formed having an intake valve 124 with a length of hollow flexible tubing. Preferably, the intake valve prevents urine from flowing back from the chamber into the urine conduit. The hollow flexible tubing has an adjustable connector 126 that can be attached to the urine conduit. Typically, the urine conduit is a long hollow flexible tube connected to an external or internal catheter. The adjustable connector 126 receives the tubing and forms a tight leak-proof seal with the tubing.

At the bottom 106, and preferably on the front 108 of the chamber 102, a drain opening 120 is formed having a drain valve 128 with a length of hollow flexible tubing. To foster draining, the device preferably has a sloping portion 140 and a drain catch 142 at the bottom of the chamber. The sloping portions, extending from both securing flange, 112 and 114, decline, relative to the top 104 and both securing flange, to the drain catch. The drain catch 142 further declines from the sloping portions and forms a rounded sink to catch collected urine. The drain opening 120 is preferably located at the drain catch of the chamber 102. The sloping portions direct the urine towards the drain catch, ensuring that all the collected urine collects near the drain opening.

The drain valve 128 prevents urine leakage. The flow of urine draining is controlled by the individual with the drain valve. Typical drain valves used include check valves and the like. Preferably, in addition to the drain valve, a drain clamp 132 and a drain cap 130 are fitted to the hollow flexible tubing. To prevent accidental loss of the drain cap, the drain cap has an attachment 136 that is secured to the flexible tubing and maintains the drain cap proximate the flexible tubing when the drain cap is disengaged with the end of the flexible tubing. The drain clamp and drain cap prevent accidental urine leakage, especially in case of drain valve failure. The hollow flexible tubing preferably has a length that allows the individual to discharge the urine in traditional urinating positions, i.e., standing for males and sitting down for females. The length of the hollow flexible tubing should be long enough for male individuals to pass the tubing through the opened zipper or fly of his shorts, swimsuit or pants while standing in the urinating position at a urinal. The drain valve and hollow flexible tubing is preferred to be secured to the chamber between draining sessions while the device is worn. The drain clamp 132 is fixed along the bottom seal of the chamber and retains the tubing while completely clamping and crimping off the tubing.

Preferably, a cloth 134 is bonded to the back side 110 of the device 100, i.e., the side of the bag that contacts the individual's skin. The cloth increases an individual's comfort by decreasing perspiration and chaffing. In addition to preventing skin irritation, the material selected for the cloth 134 is usually a fabric material that aids gripping the individual's skin to improve securing the device to the individual. The device also preferably has rounded corners 144. Rounded corners and soft edges are preferred because sharp corners and edges, especially during physical activities, can pinch the skin of the individual causing much pain and discomfort to the individual.

The device is preferably secured horizontally, relative to the leg, to the upper thigh. Such orientation completely conceals the device when worn under shorts, short skirts or swimming trunks. Securing the device to the individual can be accomplished by a number of fastening means. Preferably, a combination of straps 300 and adjustable buckles 200 is used to secure the device to the individual's thigh. The adjustable buckles have a button 202 and strap slots 204. The button 202 is sized, accordingly, to engage with the button slots 116 of the securing flange 112 and 114. The engagement between the button slots and the button should be such that the device can be easily removed and secured by the individual. The straps 300 are preferably a fabric elastic material. Additionally, the strap material chosen should be a material that minimizes skin irritation. Each end of the strap 300 is woven through a corresponding adjustable buckle 200 through the strap slots 204. The strap should be woven through the strap slots such that the strap end forms excess strap 204. The individual can tighten or loosen the excess strap to adjust the device to the individual's particular comfort. Fabric elastic straps also prevent crimping of the chamber 102. Specifically, fabric elastic straps prevent the intake opening 118 and valve 124 from crimping, which frequently occurs with adjustable rubber straps.

Although various embodiments which incorporate the teachings of the present invention have been shown and described in detail herein, those skilled in the art can readily devise many other varied embodiments that still incorporate those teachings.

What is claimed is:

1. A urine collection and drainage device comprising:
   a top and a bottom, said top and said bottom each having a vertical height;
   a first end and a second end, said first end and said second end each having a horizontal length greater than each vertical height of said top and said bottom;
   a chamber for collecting urine, said chamber being generally rectangular and having rounded corners for preventing sloshing of collected urine in said chamber;
   an intake opening in the chamber, for attaching to a urine conduit;
   a drain opening in the chamber opposite said intake opening;

a drain valve, attached at the drain opening, for controllably draining collected urine;

a plurality of sets of two baffles located in the chamber, each set of two baffles spaced equally apart from one another in said chamber; and securing means, coupled to the chamber, to secure the urine collection and drainage device in a horizontal position relative to an upper thigh of an individual's leg.

2. The urine collection and drainage device of claim 1 wherein the securing means further comprises:

a securing flange, proximate the chamber, having a button slot;

an adjustable buckle having a button and a strap slot, the button is removably engaged with the button slot of the securing flange; and a strap, woven through the strap slot of the adjustable buckle.

3. The urine collection and drainage device of claim 1 wherein the chamber further comprises:

a lower sheet; and an upper sheet, peripherally bonded to the lower sheet, and intermittently bonded to the lower sheet forming the baffle.

4. The urinary collection and drainage device of claim 1 wherein the intake opening has an intake valve.

5. The urine collection and drainage device of claim 1 wherein the chamber further comprises:

a sloping portion; and a drain catch, adjacent the sloping portion and proximate the drain opening.

6. The urinary collection and drainage device of claim 1 wherein the drain valve has a drain cap.

7. The urinary collection and drainage device of claim 1 further comprising:

a clamp for removably retaining and clamping the drain valve proximate the chamber.

8. The urine collection and drainage device of claim 1 further comprising:

a cloth, bonded to the device.

9. A urine collection and drainage device comprising:

a top and a bottom, said top and said bottom each having a vertical height;

a front side and a back side;

a first end and a second end, said first end and said second end each having a horizontal length greater than each vertical height of said top and said bottom;

securing flange at the first end and the second end, having rounded corners;

a chamber, ranging from the top and he bottom and extending from the securing flange of the first end to the securing flange of the second end, having an intake opening near the top on the front side, a drain opening near the bottom on the front side, a sloping portion along the bottom, and an outwardly extending semicircular drain catch adjacent the sloping portion and proximate the drain opening and providing a rounded sink for catching collected urine in the chamber, said intake opening opposite said drain opening, said chamber being generally rectangular and having outwardly rounded corners for preventing sloshing of collected urine in the chamber;

a plurality of sets of two baffles, located in the chamber, for preventing sloshing of collected urine in the chamber, said two baffles in each set aligned linearly and perpendicularly with respect to said top and bottom and each set of two baffles spaced equally apart from one another in the chamber and with respect to said first end and said second end;

an intake valve, attached at the intake opening of the chamber, for attachment with a urine conduit;

a drain valve, attached at the drain opening, for controllably draining collected urine;

a drain cap, removably secured to the drain valve;

a clamp for removably retaining and clamping the drain valve proximate the chamber;

a cloth, bonded to the back side;

a button slot formed in each securing flange;

an adjustable buckle having a button and a strap slot, the button is removably engaged with button slot of the securing flange; and a strap, woven through the strap slot of the adjustable buckle, adjustably positioned to secure the urine collection and drainage device in a horizontal position relative to an upper thigh of an individual's leg.

* * * * *